(12) United States Patent
Hangartner et al.

(10) Patent No.: US 7,488,109 B2
(45) Date of Patent: Feb. 10, 2009

(54) OSTEOPOROSIS SCREENING USING RADIOGRAPHIC ABSORPTIOMETRY OF THE MANDIBLE

(75) Inventors: Thomas Niklaus Hangartner, Dayton, OH (US); Julie Ann Skipper, Dayton, OH (US)

(73) Assignee: Wright State University, Dayton, OH (US)

( * ) Notice: Subject to any disclaimer, the term of this patent is extended or adjusted under 35 U.S.C. 154(b) by 20 days.

(21) Appl. No.: 10/550,668

(22) PCT Filed: Mar. 27, 2003

(86) PCT No.: PCT/US03/09418

§ 371 (c)(1), (2), (4) Date: Feb. 21, 2007

(87) PCT Pub. No.: WO2004/096048

PCT Pub. Date: Nov. 11, 2004

(65) Prior Publication Data

US 2007/0133739 A1 Jun. 14, 2007

(51) Int. Cl.
*G01D 18/00* (2006.01)
(52) U.S. Cl. .................... 378/207; 378/168
(58) Field of Classification Search ........... 378/207, 378/168–170
See application file for complete search history.

(56) References Cited

U.S. PATENT DOCUMENTS

| | | | |
|---|---|---|---|
| 5,187,731 A | 2/1993 | Shimura | |
| 5,544,157 A | 8/1996 | Wenstrup et al. | |
| 5,784,433 A | 7/1998 | Higa | |
| 5,852,647 A | 12/1998 | Schick et al. | |
| D406,892 S | 3/1999 | Warren | |
| D407,158 S | 3/1999 | Rubinstein | |
| 5,915,036 A | 6/1999 | Grunkin et al. | |
| 6,205,348 B1 | 3/2001 | Giger et al. | |
| 6,320,931 B1 | 11/2001 | Arnold | |
| 6,324,252 B2 | 11/2001 | Siffert et al. | |
| 6,343,875 B1 | 2/2002 | Eppinger et al. | |
| 6,381,301 B1 | 4/2002 | Massie | |
| 6,690,761 B2 | 2/2004 | Lang et al. | |
| 6,904,123 B2 | 6/2005 | Lang | |
| 2002/0067798 A1 | 6/2002 | Lang | |
| 2002/0150205 A1 | 10/2002 | Adriaansz | |
| 2002/0154733 A1 | 10/2002 | Massie | |
| 2003/0015208 A1 | 1/2003 | Lang et al. | |
| 2003/0063704 A1* | 4/2003 | Lang ........................... 378/54 | |
| 2003/0112921 A1 | 6/2003 | Lang et al. | |

OTHER PUBLICATIONS

Investigator Abstracts Biomedical Engineering, Biomedical Engineering Research Grants Apr. 1999, Theresa Atkinson, Ph. D. Assistant Professor, Department of Mechanical Engineering Wayne State University (RG-98-0530) Detroit, MI.

(Continued)

*Primary Examiner*—Hoon Song
(74) *Attorney, Agent, or Firm*—Dinsmore & Shohl LLP

(57) ABSTRACT

A dental radiographic absorptiometric device and method is provided that quantitatively measures the amount of bone of a patient in any dentist's office. Absorptiometric information simultaneously obtained from the mandible and calibration devices are used to screen patients for osteoporosis.

35 Claims, 4 Drawing Sheets

OTHER PUBLICATIONS

Michaeli et al., A New X-Ray Based Osteoporosis Screening Tool Provides Accurate and Precise Assessment of Phalanx Bone Mineral Contect, Jounal of Clinical Densitometry vol. 2, No. 1 23-30 Winter 1998.

Tambe et al., Analysis of dental X-ray images, "Extraction of trabecu from panoramic X-ray images of gnathic bone," 2001 General Conference, The Institute of Electronics, Information and Communication Engineers.

Homer et al., Mandibular bone mineral density as a predictor of skeletal osteoporosis, 1996 The British Journal of Radiology vol. 69. No. 827.

Colbert et al., Radiographic Absorptiometry (Photodensitometry), Survey of Phalangeal Bone Mineral Density and Bone Sizes in a Sample Population of 50 Hemodialysis Patients, Internal Report, Radiological Research Laboratory, Yellow Springs, Ohio, Dec. 5, 1978.

MSc Project: Detection of Osteoporosis from Dental Radiographs., The University of Manchester copyright 2001.

Yang et al, "Radiographic Absorptiometry for Bone Mineral Measurement of the Phalanges: Precision and Accuracy Study" Radiology Sep. 1994, 192:857-859.

Seq # 126—Epidemiology and Quality of Life, 3:45 PM-5:00 PM, Mar. 7, 2002 San Diego Convention Center Exhibit Hall.

* cited by examiner

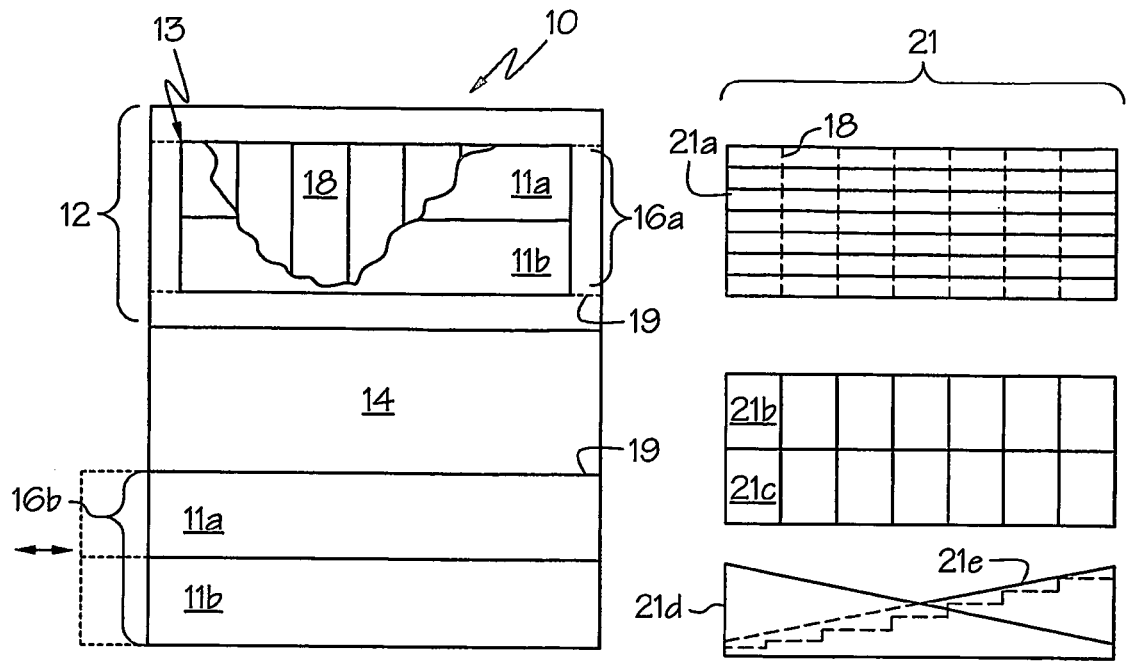
FIG. 1A
FIG. 1C
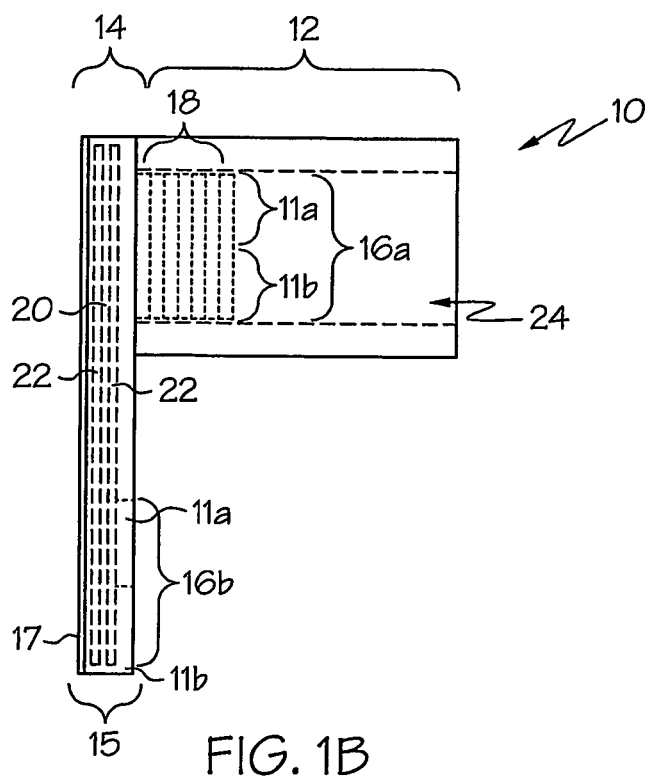
FIG. 1B

OSTEOPOROSIS SCREENING USING RADIOGRAPHIC ABSORPTIOMETRY OF THE MANDIBLE

The present invention relates to preventive medicine and in particular, but not limited, to a method and system using radiographic absorptiometry of the mandible for osteoporosis screening.

Currently, osteoporosis affects approximately 50 percent of women and 20 percent of men over the age of 50 in the US. Additionally, osteoporosis occurs sooner if the amount of bone established at maturity is less than average. Compounding this problem, osteoporosis is typically not discovered early enough for treatment to have the best chance for success. Until the present invention, routine X-rays have been a poor predictor for osteoporosis, as prior art methods have only had the ability to show osteopenia once 20 to 30 percent of bone mass is lost, which is considerably late in the course of the disease.

Bone is composed of a mixture of high-turnover trabecular (spongy) bone and slowly changing cortical (compact) bone. Osteoporosis is a bone disease that reduces the amount of bone. This reduction results in an overall weakening of the affected bones and an increased risk of hip and vertebral fractures. Such fractures involve considerable socioeconomic implications in that they cause severe pain, immobility, and often result in surgery, wherein 25 to 30 percent of patients undergoing hip surgery die within five years of having this operation.

Bone mineral density (BMD) is a useful predictor of bone strength and indirectly of fracture risk. Bone mineral density is usually reported as the standard deviation compared to either peak bone mass (T-score) or compared to age matched controls (Z-score). The World Health Organization defines osteopenia as bone mass that is from $-1$ to $-2.5$ standard deviations (S.D.) of peak bone mass and osteoporosis as bone mass that is below $-2.5$ standard deviations of peak bone mass. Typically, in clinical practice, bone mineral densitometry is performed at target sites such as the lumbar spine (L1-L4) and the hip (femoral neck), which are sites particularly susceptible to osteoporotic fractures. At those target sites, bone mineral densitometry provides a measure of the amount of bone and thus an indication of whether the patient is suffering from osteoporosis, since in osteoporosis there is a proportional loss of both matrix and material. As a rule of thumb, the fracture risk is doubled for each standard deviation below the peak bone mass. This increases exponentially, so the fracture risk is four times greater at $-2$ S.D. and eight times greater at $-3$ S.D.

Currently, dual energy X-ray absorptiometry (DXA) and quantitative computed tomography (QCT) are the BMD tests of choice for diagnosing osteoporosis. Although the availability of DXA and QCT devices has increased over the last decade, only a small percentage of the population undergoes BMD testing to facilitate early detection of osteoporosis. The associated expense (e.g., equipment cost, dedicated space, and personnel) is a major reason for the lack of BMD testing. Another is the inconvenience of its use as a preventive medicine tool, which requires a separate appointment and trip to a testing facility. Additionally, DXA and QCT testing must follow complex protocols, which are poorly reproduced in a community setting. Accordingly, there is a need for an inexpensive screening method for osteoporosis that may be performed easily and routinely for the overall benefit of the patient and society.

The present invention is a method and apparatus providing for the inexpensive screening for osteoporosis using conventional dental X-ray equipment. Dentists are currently the only healthcare providers whom patients regularly see, even if they are not ill, making the dental office environment an ideal mass-screening setting for osteoporosis. Additionally, the wide availability of dental X-ray equipment as well as its initial low cost and low cost of use creates an inexpensive screening method for osteoporosis, which may be performed easily and routinely for the overall benefit of the patient and society.

The inventors have conducted a pilot study designed to 1) evaluate the range of mandible size, density and homogeneity in the general population and 2) assess a custom calibration wedge as a means of normalizing radiographs for varying exposure and film development conditions. The X-ray exposure parameters were maintained constant for all subjects. Periapical radiographs of a selected region of interest, such as the posterior mandible, and a calibration element were simultaneously acquired under single-energy and dual-energy conditions.

The patients of the pilot study group fell into the following categories: I (female, age 25-35), II (male, age 25-35), III (female, age 50+), IV (male, age 60+) and V (persons at high risk for osteoporosis). Using the device of the present invention, a significant difference in mandibular BMD between Categories III and V ($p=0.1$) was detected. Additionally, mandibular BMDs were positively correlated with a body mass index ($R=0.55$, $p-0.005$) and shown to decrease with age. Furthermore, as BMD decreased, increased variance within the regions of interests (ROIs) was observed. A typical number for correlation of bone mineral density at different sites in the body (e.g., lumbar vertebrae and hip, hip and radius) is about 0.7. The values obtained by the present invention in the selected ROIs have been similarly correlated with the spine and hip, confirming that the selected ROIs of the pilot study meet the criteria of having a large percentage of trabecular bone.

The benefits of the present invention are the opportunistic screening in a setting where equipment exists and people visit, an optimized dual-energy measurement that reduces inaccuracies due to soft tissue effects, and a well-calibrated measurement. This information can be used by a physician to diagnose osteoporosis and recommend treatment strategies.

In one aspect of the present invention provided is a method to screen for osteoporosis damage to a patient's bones. The method comprises placing in the mouth of the patient adjacent to a mandibular bone being tested, a dental radiographic absorptiometric device comprising at least one calibration element. X-ray energy is applied to the dental radiographic absorptiometric device simultaneously through the mandibular bone and the calibration element to generate both a bone absorptive record from the mandibular bone and a calibration element absorptive record from the calibration element. The bone absorptive record is analyzed against the calibration element absorptive record to determine the extent, if any, of the osteoporosis damage to the mandibular bone.

In another aspect of the invention provided is one embodiment of a dental radiographic absorptiometric device adapted for osteoporosis screening using a standard dental X-ray machine and being locatable in a patient's mouth. The device comprises an image portion having a first surface, and a biting block portion attached to the first surface of the image portion. The biting block portion defines a cavity, and at least one calibration element is accommodated in the cavity of the biting block portion.

Further provided is another embodiment of a dental radiographic absorptiometric device adapted for osteoporosis screening using a standard dental X-ray machine and being locatable in a patient's mouth. The device comprises an image portion having a first surface, and a biting block portion attached to the first surface of the image portion. The biting block portion defines a cavity, and at least one calibration element and at least one of an upper beam filter are accommodated in the cavity of the biting block portion. The device also includes at least one of a lower beam filter provided to the imaging portion below the biting block portion.

These and other features and objects of the present invention will be apparent in light of the description of the invention embodied herein.

The following detailed description of the embodiments of the present invention can be best understood when read in conjunction with the following drawings, where like structure is indicated with like reference numerals and in which:

FIG. 1A is a front illustration view, partially cutaway, of the nondigital embodiment of a dental radiographic absorptiometric device according to the present invention;

FIG. 1B is a side illustration view of the non-digital embodiment of FIG. 1A;

FIG. 1C are illustrations of calibration wedge arrangements suitable for use with the embodiment of FIG. 1A;

Figure 2:
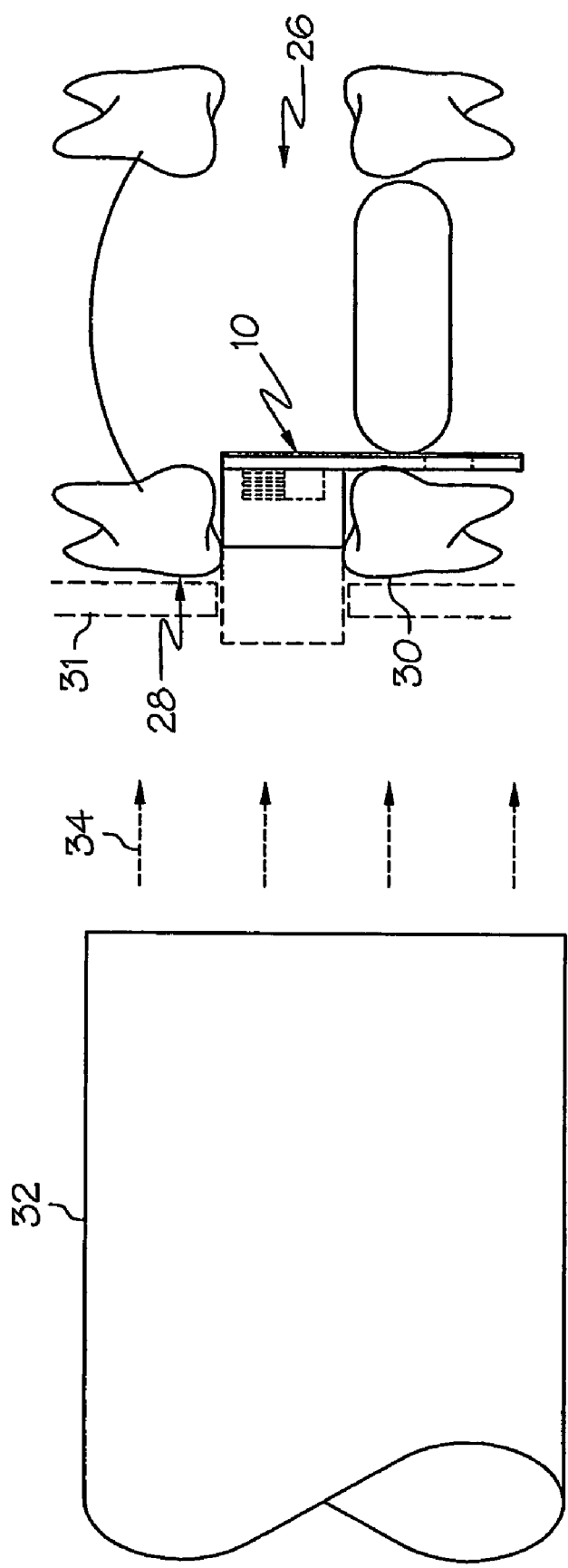
FIG. 2 is an illustration of the non-digital device according to the present invention situated in the mouth of a patient and being radiated by X-rays from a conventional dental X-ray machine.

The present invention provides an opportunistic approach to osteoporosis screening at the time of routine check-ups in the dental health care setting using radiographic absorptiometry. In particular, radiographic absorptiometric measurements of the mandible are taken using a dental radiographic absorptiometric device to determine the amount or net bone structure inside the bone that an X-ray beam from a standard dental X-ray machine penetrates. The present invention may be applied to either non-digital or digital radiographic absorptiometry.

Referring to FIGS. 1A and 1B, illustrated are front and side views, respectively, of a non-digital embodiment of a dental radiographic absorptiometric device 10 according to the present invention. The non-digital device 10 is adapted to take periapical radiographs of a patient. In the illustrated embodiment, the non-digital device 10 is generally rectangular and may be provided in a number of sizes to easily fit in an adult mouth. The non-digital device 10 comprises a biting portion 12 to allow the patient to bite down so motion is less problematic, and an imaging portion 14. The biting portion 12 includes, generally shown, a calibration element 13, which includes a upper beam filter 16a and a calibration wedge 18. The device 10 further includes a lower beam filter 16b provided to image portion 14 below the biting portion 12. The beam filters 16a and 16b are optimized in material and thickness to provide, in combination with the calibration wedge 18, a radiographic image of the mandible that permits early evaluation of a patient for osteoporosis.

Although the non-digital device 10, the beam filters 16a and 16b, and the calibration wedge 18 are all illustrated as rectangular, other geometric shapes may be used. Furthermore, although the illustrated non-digital device 10 is configured for a dual-energy measurement, as will be explained hereafter, the non-digital device is suitable for a single-energy measurement using calibration wedge 18 with or without beam filters 16a and/or 16b.

The biting portion 12 of the non-digital device 10 is a relatively thick rectangular structure and is either integral with the imaging portion 14, or mounts thereon. The imaging portion 14 is a relatively thin rectangular structure comprising a base layer 15 and a removable cover layer 17. The base layer 15 is in the path of the X-rays and adds to the X-ray attenuation. The cover layer 17 is removably attached to the base layer 15 to provide an enclosure for accommodating a standard periapical radiographic film 20. The biting portion 12 and imaging portion 14 are made of polycarbonate, plastic, acrylic, methyl methacrylate, any other suitable low attenuating materials, and combinations thereof.

The beam filters 16a and 16b are provided in upper and lower portions of device 10 to spectrally filter the output of the X-ray source into two distinct X-ray spectra and to provide an optimized dual-energy measurement, which reduces inaccuracies due to soft tissue effects. As illustrated, the upper beam filter 16a is provided in front of the calibration wedge 18. Alternatively, the upper beam filters 16a may be provided behind the calibration wedge 18, if desired. The upper beam filter 16a comprises a first pair of filters 11a and 11b. In the lower portion of device 10, the lower beam filter 16b comprises a second pair of filter 11a and 11b, which substantially span the width of the imaging portion 14 in a side-by-side orientation. These first and second pairs of filters 11a and 11b simultaneously yield adjacent higher and lower energy images in both upper and lower portions of film 20 for comparative assessment of relative optical densities.

Filters 11 and 11b are each a thin sheet material having a thickness of about 0.05 mm to about 0.12 mm. In particular, filters 11a and 11b each comprises a material selected from cerium, molybdenum, any other suitable material, and combinations thereof. In one specific embodiment, the first filter 11a is 0.075 mm Ce and the second filter 11b is 0.10 mm Mo; however, in other embodiments varying number of suitable filters with varying thicknesses and similar atomic numbers may be used. It is to be appreciated that the thickness of filter materials is dependant on atomic number, kilo-voltage settings of the dental X-ray machine, and the desired filtration factor. For example, a dental X-ray machine setting in the range from about 60 kVp to about 80 kVp is suitable for taking mandible measurements using the above-mentioned beam filter thicknesses and materials. If desired, the non-digital device 10 may be conveniently configured to permit the exchanging of beam filters of various thicknesses and materials, which is generally illustrated by a side-to-side arrow, such as for example, via slots 19 provided in the device 10.

In the illustrated embodiment of FIGS. 1A and 1B, the calibration wedge 18 is provided in a cavity 24 of the biting portion 12, and is situated adjacent to the base layer 15 of the imaging portion 14. The calibration wedge 18 is made of copper, its alloys, and any other suitable material and provides a series and/or gradient of incrementally changing contrast test objects. In this manner, with each exposure of the non-digital device 10, the calibration wedge 18 provides calibration data to film 20.

In one embodiment, the calibration wedge 18 is a step wedge, or alternatively, a smooth tapered wedge, such as wedge 21d. In the illustrated embodiment, seven-steps are used, which changes the image contrast by approximately 14.3% per step. If desired, finer or coarser contrast increments may be provided with more or fewer steps, respectively. In particular, the calibration wedge 18 has dimensions of about 3 mm by about 25 mm and has steps of thicknesses ranging from about 0.05 mm to 0.33 mm. In other embodiments, the wedge dimension and step thicknesses may vary somewhat and still provide sufficient contrast to calibrate the resulting image on film 20.

If desired, a set of wedges 21 may be used to provide high and low energy calibration references, in which a number of such calibration arrangements are illustrated by FIG. 1C. In one embodiment, the set of wedges 21 comprises overlaying wedge 18 with another wedge 21a in a crisscross arrangement. In another embodiment, the set of wedges 21 comprise a calibration wedge 21b provided adjacently to another calibration wedge 21c in a side-by-side orientation. In still another embodiment, the set of wedges 21 comprises a calibration wedge 21d provided adjacently to another calibration wedge 21e in a counter side-by-side orientation. The wedges may be a smooth (tapered) or step wedge. Additionally, in the embodiments using the set of wedges 21, one wedge may comprise acrylic for a soft tissue reference, and the other wedge may comprise copper or aluminum for a bone tissue reference. The set of wedges 21 can similarly be inserted into cavity 24 of the biting portion 12, if so used.

The calibration wedge 18 provides a "gray scale" image of objects with known absorption differences, which allows the image analysis system to analyze the exposed film. It is to be appreciated that the calibration of individual films is very important. Variability in acquisition parameters can significantly affect the measured values. When radiographic exposures are made, the X-ray tube settings, patient size and patient composition (lean mass vs. fat) play a role in the resultant lightness or darkness of the film. Further, film development, chemical age and temperature affect film intensity values. Therefore, each film is normalized against a standard provided by the calibration wedge 18 in order to adjust for differences among X-ray equipments, exposures, types of film, and the development process. Additionally, the calibration wedge 18 can be used as part of a quality control procedure to evaluate the dental equipment at each screening site.

The film 20 has an optical density that varies systematically, e.g., logarithmically, in accordance with the amount of radiation exposure. To increase its efficiency and lower the required dosage of X-rays, the film 20 optionally can be sandwiched between sheets of plastic called intensifying screens 22. Each intensifying screen 22 is a plastic base coated with an X-ray sensitive phosphor and which converts X-rays into light to produce the latent image on the film 20.

Referring to FIG. 2, the non-digital device 10 is conveniently used with traditional dental radiography. In one embodiment, osteoporosis screening is performed by imaging the mandible using standard dental X-ray equipment and standard dental film. Since osteoporosis is a generalized disease, its effects are not limited to the spine and hip. Since osteoporotic bone loss is mainly a result of hormonal changes, it has been found that osteoporotic patients show bone loss also in the mandible.

In operation, the non-digital device 10 is introduced at the proper location within the patient's mouth 26, and the patient is instructed to bite down on the biting portion 12 between corresponding upper and lower teeth 28 and 30. Ideally, a perpendicular orientation between a X-ray position indicating device (or simply "cone") 32 and the non-digital device 10 will be maintained with respect to a line of sight 34 for X-rays emanating from the cone 32 to eliminate distortions, improper focus-and the like. If desired, an aiming device (not shown) provided to cone 32 can conveniently be used with the non-digital device 10 of the present invention.

The biting portion 12 is dimensioned to fit in between the upper and lower teeth 28 and 30, such that the patient may close his or her mouth. Optionally, however, the biting portion 12 may be sized to extend outwardly from the patient's mouth such that the cheek and/or lips 31 of the patient do not come between the X-ray source, the calibration element 13, and the portion of the film 20 situated behind the calibration element. By this arrangement, a portion of the film is unaffected by the soft tissue effect and provides an accurate normalized reference for each exposure.

Figure 3:
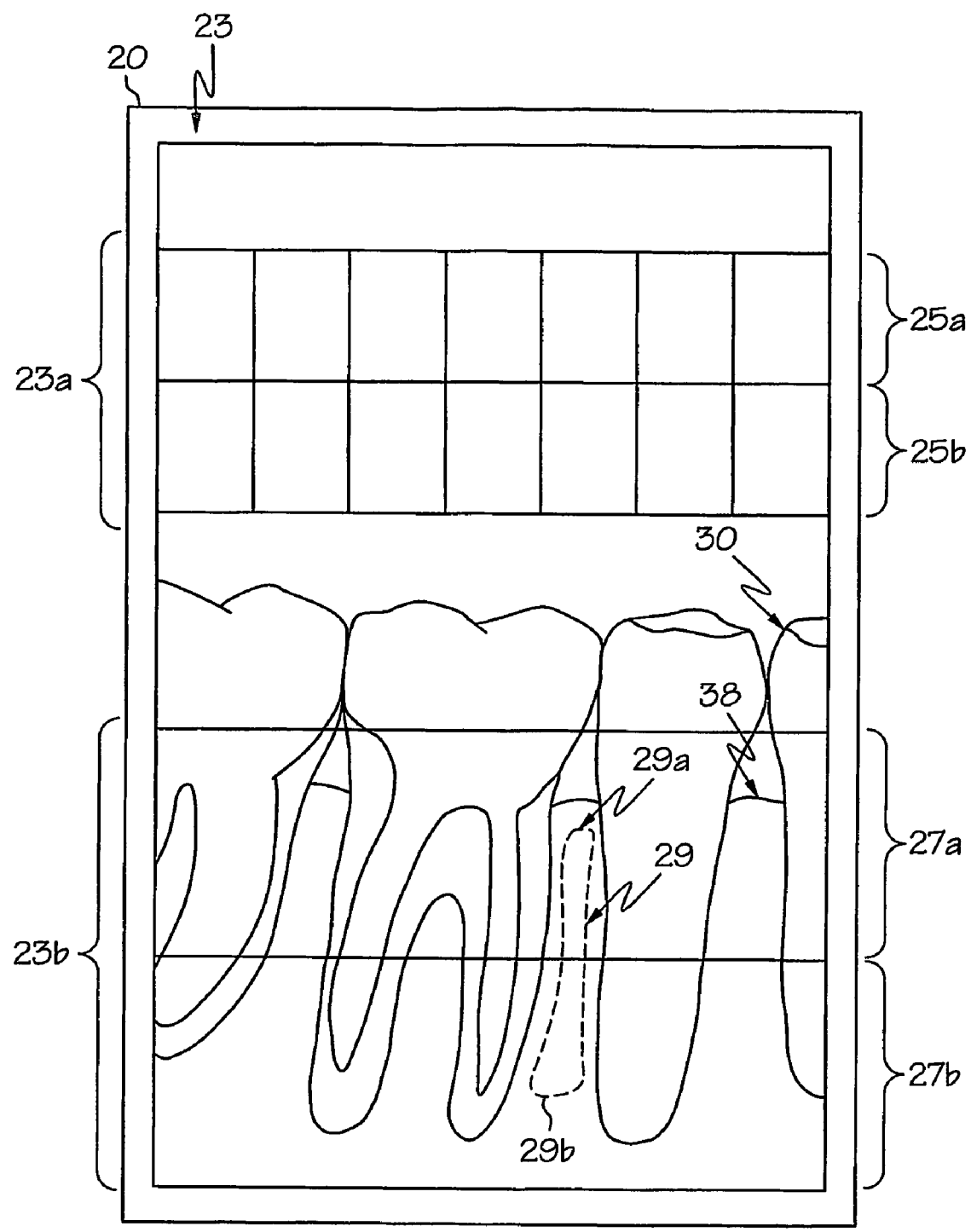
FIG. 3 shows an X-ray image in accordance with the present invention showing calibration data, filtered bone mineral density readings, and a predetermined region of interest; and, FIGS. 4A and 4B are front and side illustration views, respectively, of a digital embodiment of a dental radiographic absorptiometric device according to the present invention.

When X-rays pass through the patient's mouth 26 during a dental exam, more X-rays are absorbed by the denser parts (such as teeth and bone) than by soft tissues (such as cheeks and gums) before striking film 20, and creating an image thereon. As illustrated by FIG. 3, which is an example of a mandibular radiographic image according to the present invention, the molars of the lower teeth 30 will appear lighter because fewer X-rays penetrate to reach the film 20. The calibration element 13 provided above the teeth and gums will appear to have a varying degree of darkness because each progressive rectangular portion of the calibration wedge 18 permits more X-ray penetration. The calibration element 13 is therefore used for determining energy distribution and attenuation coefficients.

In one embodiment, the mandible is used as the bone measurement site. In another embodiment, the trabecular bone in the area between the roots of the second bicuspid and the first molar and from the superior border of the mandible to approximately one-half of the molar root length is designated as the region of interest (RIO) 29 for these measurements. Other ROIs between other teeth or roots also may be selected and advantageously used with the present invention. In particular, analysis locations could be chosen where the variance of optical density values could be related to the progression of bone loss.

After imaging using a low x-ray dose, the resulting image 23 on film 20 is subsequently analyzed for optical values (e.g., pixel grayscale values) relating to calibration and bone equivalent densities. This analysis can be automated by digitizing the image 23 on the film 20 with a film digitizer. The resulting optical values extracted by the film digitizer can then be analyzed using an algorithm that subtracts the soft-tissue effects from the digitized images and compares the intensities of the bone and the calibration wedge at specific locations to determine bone density and bone mineral content. The result of this analysis may be used to classify a patient's BMD as either "normal" or "below normal" at the specific bone measurement site locations, which can be used as a recommendation to seek further diagnosis or treatment.

In a dual-energy embodiment, calibration values are extracted from an upper portion 23a of the resulting image 23. As illustrated, the upper portion 23a is divided into upper and lower regions 25a and 25b, which corresponds to the portions of the film 20 located behind the first (upper) pair of filters 11a and 11b and calibration wedge 18. As with the upper portion 23a, the lower portion 23b of the resulting image 23 is divided into upper and lower regions 27a and 27b, which corresponds to the portions of the film 20 located behind the second (lower) pair of filters 11a and 11b. Since the beam filters 16a and 16b are same in both the biting and imaging portions 12 and 14 of the device 10, the upper region 27a of the lower portion 23b is exposed to the same energy level as the upper region 25a of the upper portion 23a during imaging. Likewise, the lower region 27b of the lower portion 23b is exposed to the same energy level as the lower region 25b on the upper portion 23a. In this manner, dual-energy images and calibration data is provided concurrently on film 20.

Hard tissue mass is determined from the dual-energy images and calibration data provided on film 20. At a point on the high-energy calibration wedge image where the optical density is identical to that of the high-energy mandible image, the following equation applies:

$$e^{-\mu_{W\!H}(E)d_W} = e^{-(\mu_{SH}(E)d_S + \mu_{BH}(E)d_B)}$$

A second similar equation can be created with the corresponding low-energy data:

$$e^{-\mu_{W\!L}(E)d_W} = e^{-(\mu_{SL}(E)d_S + \mu_{BL}(E)d_B)}$$

where $d_W$ is the wedge thickness, $d_S$ is the soft tissue thickness, $d_B$ is the bone thickness, and $\mu_W$, $\mu_S$, and $\mu_B$ are the energy-dependent linear attenuation coefficients for the wedge material(s), soft tissue and bone, respectively. The subscripts L and H refer to low-energy and high-energy values. Since the wedge thickness at each step is known and attenuation coefficient values for the wedge material(s), bone and soft tissue are available in the literature, the only unknowns are the bone and soft tissue thicknesses dB and ds, which are easily solved using conventional techniques. Of course, although only specific wedge optical density values corresponding to the individual steps are available from the image data, the wedge-equivalent thickness for any optical density may be found using appropriate interpolation techniques.

As previously mentioned, device 10 can be provided with or without beam filters 16a and/or 16b and used with a single-energy. In such a single-energy embodiment, the pixel values in the region of interest are extracted and averaged. The resulting average value is then compared to a calibration curve generated from extracted calibration wedge values from the image 23 on film 20 to yield an equivalency density value. For example, a young person might have an equivalent bone mineral density in the mandible of 240 microns of copper whereas an osteoporotic patient's value might be equivalent to 100 microns of copper.

It is to be appreciated that the disclosed pilot study mentioned in the summary of the invention validated the device 10 using a single-energy and the disclosed thickness range of the copper step wedge. In particular, patient bone mineral densities (BMDs) were assessed using a film algorithm, which correlated optical density (OD) to BMD determinations in mandibular measurements from the selected region-of-interest 29 (FIG. 3). Based on over 100 irradiations, dozens of calibration curves were developed and incorporated in the film algorithm. It is envisioned that further data will be obtained from a large, population-based study for determining the distribution of mandibular bone mineral density values, expressed in units of copper-equivalency, for all types of patient classifications.

The present invention also includes an automated image analysis process that outlines the regions of interest and teeth. Such an embodiment is comprised of an image digitization component and an automated image analysis component. Radiographs of the mandible and the calibration wedges are acquired and digitized following the above-mentioned procedure. As illustrated also by FIG. 3, teeth 30, bone and soft tissue 38, and a region of interest 29 are outlined on a digitized image of the film 20 by the image analysis component, which then provides computed density values of each of these regions relative to the density of the calibration wedge.

Figure 4A:
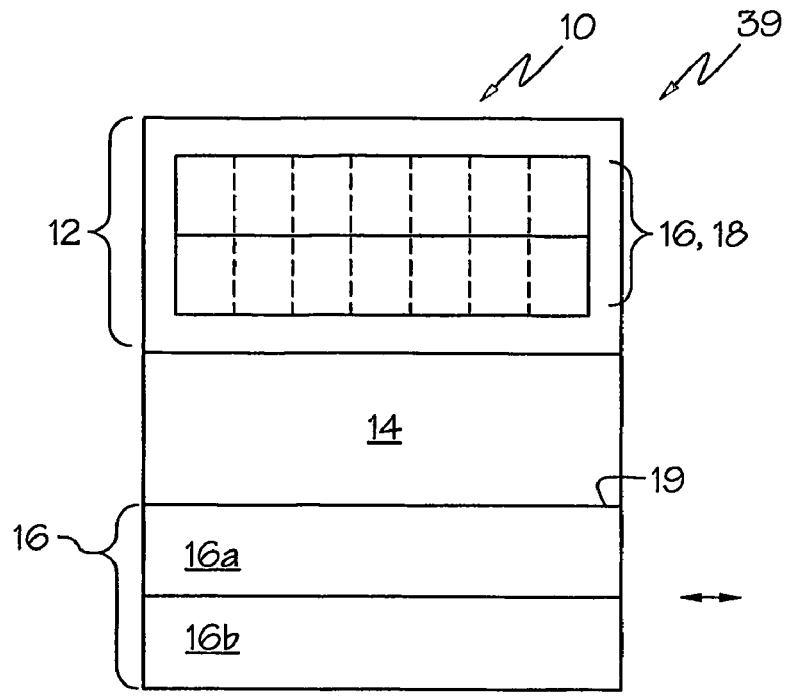
Figure 4B:
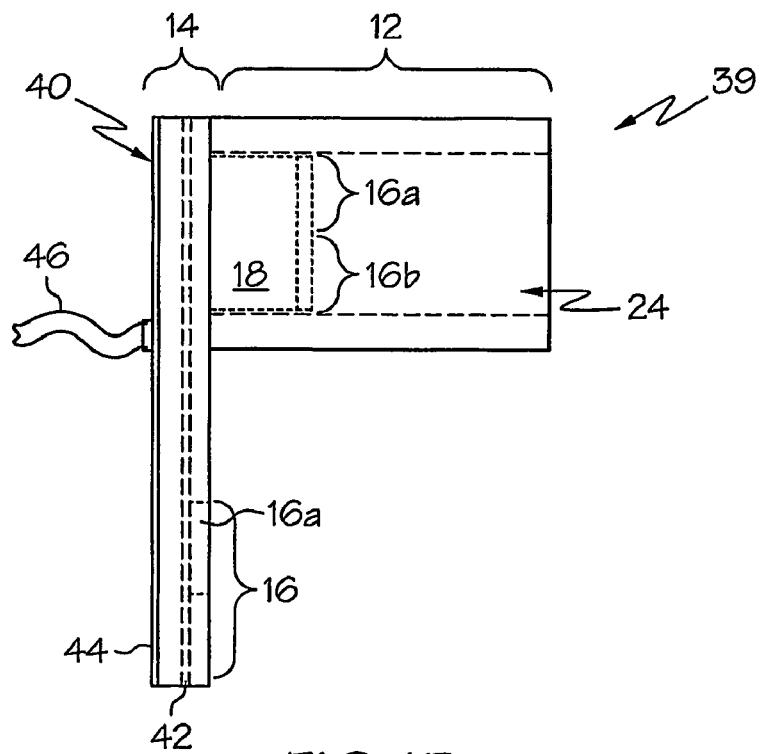

Referring to FIGS. 4A and 4B, illustrated are front and side views, respectively, of a digital embodiment of a dental radiographic absorptiometric device 39 according to the present invention. In a digital radiography embodiment, the dental film 20 (FIG. 1B) is replaced with digital sensors 40. After each exposure, an image is provided on a computer screen. The images are conveniently stored in computer memory, from which they can be easily retrieved, combined, and manipulated to supply more information. The chemical waste associated with film processing is eliminated, and most significantly, patients are exposed to much less of the X-ray dosage typically delivered in the nondigital embodiment.

It is to be appreciated that the primary difference between digital radiographic absorptiometry (DRA) and its non-digital predecessor is that the image capture, display and analysis functions are performed by one system at a physician's site, without the use of X-ray film. In the DRA embodiment, calibration wedges 18 and beam filters 16 are still used in conjunction with the biting portion 12. The digital sensor 40 may comprise a phosphor screen 42 and a charge-coupled device (CCD) camera 44, CMOS wafers, or any other suitable electronic sensor. As with the non-digital device 10, the digital device 39 is placed in the patient's mouth and irradiated by the X-ray source. Visible photons emitted from the phosphor screen 42 are collected and imaged by the charge-coupled device camera 44. The camera's digital output, via a wire 46, is sent to a PC, which analyzes the image for bone density and bone mineral content in real-time using the same above-mentioned optical scanning techniques.

While the invention has been particularly shown and described with reference to the preferred embodiments thereof, it will be understood by those skilled in the art that various changes in form and details may be made without departing from the spirit and scope of the invention.

The invention claimed is:

1. A method to screen for osteoporosis damage to a patient's bones comprising:
   placing in the mouth of the patient adjacent to a mandibular bone being tested, a dental radiographic absorptiometric device comprising at least one calibration element and at least one beam filter;
   applying X-ray energy to said dental radiographic absorptiometric device simultaneously through said mandibular bone, said at least one beam filter and said at least one calibration element to generate both a bone absorptive record from said mandibular bone, a calibration element absorptive record from said at least one calibration element and a filtered X-ray output record from said at least one beam filter; and
   analyzing said bone absorptive record against said calibration element absorptive record and said filtered X-ray output record to determine the extent, if any, of the osteoporosis damage to said mandibular bone.

2. The method as defined in claim 1 wherein said X-ray energy is provided by a device selected from the group consisting of single-energy and dual-energy devices.

3. The method as defined in claim 1 wherein said at least one calibration element is at least one calibration wedge and at least one beam filter.

4. The method as defined in claim 1 wherein said dental radiographic absorptiometric device is selected from the group consisting of digital and non-digital radiographic absorptiometric devices.

5. The method as defined in claim 1 wherein said dental radiographic absorptiometric device is selected from the group consisting of a charge coupled device camera, CMOS wafers, electronic image sensors, and X-ray film.

6. The method as defined in claim 1 wherein said dental radiographic absorptiometric device comprises an image sensor with a fluorescent layer.

7. The method as defined in claim 1 further comprising selecting a region of interest in the mandible of the patient.

8. The method as defined in claim 1 further comprising digitizing said bone absorptive record and said calibration element absorptive record.

9. The method as defined in claim 7 wherein said region of interest is trabecular bone in the mandible.

10. The method as defined in claim 7 wherein said region of interest is trabecula in the area between roots of the second bicuspid and the first molar and from the superior border of the mandibular to approximately one-half of the molar root length.

11. The method as defined in claim 8 further comprising subtracting soft tissue effects from digital images of said bone absorptive record and said calibration element absorptive record and comparing intensities of said digital images at specific locations to determine bone density and bone mineral content.

12. The method as defined in claim 11 further comprising classifying said bone mineral content of the patient as either "normal" or "below normal" at said specific locations.

13. A dental radiographic absorptiometric device adapted for osteoporosis screening using a standard dental X-ray machine and being locatable in a patient's mouth, said device comprising:
an imaging portion having a first surface;
a biting block portion attached to the first surface of said imaging portion, said biting block portion defining a cavity;
at least one calibration element accommodated in said cavity of said biting block portion; and
at least one beam filter cooperative with at least one of said imaging portion and said biting block portion such that an X-ray emanating from said X-ray machine is broken down into distinct X-ray spectra upon interaction with said at least one beam filter.

14. The dental radiographic absorptiometric device of claim 13 wherein said imaging portion is an enclosure sized to accommodate standard dental X-ray film.

15. The dental radiographic device of claim 13 wherein said imaging portion is an electronic sensor.

16. The dental radiographic device of claim 15 wherein said electronic sensor is a CCD camera provided with a fluorescent screen.

17. The dental radiographic device of claim 15 wherein said electronic sensor is selected from the group consisting of a CMOS based x-ray sensor, a CCD based x-ray sensor, and any other suitable intraoral electronic x-ray sensors.

18. The dental radiographic device of claim 13 wherein said cavity of said biting block portion extends from said first surface of said imaging portion completely through said biting block portion.

19. The dental radiographic device of claim 13 wherein said biting block portion extends a distance from said imaging portion such that the device may be fully enclosed in the patient's mouth.

20. The dental radiographic device of claim 13 wherein said biting block portion extends a distance from said imaging portion such that the device protrudes partially from the patient's mouth.

21. The dental radiographic absorptiometric device of claim 13 wherein said biting block portion and said imaging portion is each a material selected from the group consisting of plastic, acrylic, methyl methacrylate, any other suitable low attenuating materials, and combinations thereof.

22. The dental radiographic absorptiometric device of claim 13 wherein said at least one calibration element is a material selected from the group consisting of copper, copper alloys, any other suitable calibration material, and combinations thereof.

23. The dental radiographic absorptiometric device of claim 13 wherein said at least one calibration element is selected from the group consisting of step wedges, tapered wedges, and combinations thereof.

24. The dental radiographic absorptiometric device of claim 13 wherein said at least one calibration element is a step wedge having dimensions of about 3 mm by about 25 mm, and has steps of thicknesses ranging from about 0.05 mm to about 0.33 mm.

25. The dental radiographic absorptiometric device of claim 13 wherein said at least one calibration element is two calibration wedges.

26. The dental radiographic absorptiometric device of claim 25 wherein said calibration wedges are provided in a counter side-by-side orientation.

27. The dental radiographic absorptiometric device of claim 25 wherein said calibration wedges are provided in a side-by-side orientation.

28. The dental radiographic absorptiometric device of claim 25 wherein said calibration wedges are provided in crisscross arrangement.

29. A dental radiographic absorptiometric device adapted for osteoporosis screening using a standard dental X-ray machine and being locatable in a patient's mouth, said device comprising:
an imaging portion having a first surface;
a biting block portion attached to the first surface of said imaging portion, said biting block portion defining a cavity;
at least one calibration element and at least one of an upper beam filter accommodated in said cavity of said biting block portion; and
at least one of a lower beam filter provided to said imaging portion below said biting block portion.

30. The dental radiographic absorptiometric device of claim 29 wherein said beam filters are each a material selected from the group consisting of cerium, molybdenum, any other suitable beam filtering material, and combinations thereof.

31. The dental radiographic absorptiometric device of claim 29 wherein said beam filters are each a thin sheet material having a thickness of about 0.05 mm to about 0.12 mm.

32. The dental radiographic absorptiometric device of claim 29 wherein said upper and lower beam filters each comprises first and second filters.

33. The dental radiographic absorptiometric device of claim 32 wherein said first filter is 0.075 mm Ce and said second filter is 0.10 mm Mo.

34. The dental radiographic absorptiometric device of claim 32 wherein said fist and second filters of said upper and low beam filters are provided in a side-by-side orientation.

35. The dental radiographic absorptiometric device of claim 29 wherein said upper and lower beam filters are exchangeable with other beam filters.

* * * * *